(12) United States Patent
Wang et al.

(10) Patent No.: US 11,903,923 B2
(45) Date of Patent: Feb. 20, 2024

(54) USE OF ANDROGRAPHOLIDE DERIVATIVES IN PREPARATION OF MEDICAMENTS FOR PREVENTING AND TREATING INFLAMMATORY BOWEL DISEASES

(71) Applicant: GUANGZHOU MAGPIE PHARMACEUTICALS CO., LTD., Guangzhou (CN)

(72) Inventors: Yuqiang Wang, Guangzhou (CN); Lipeng Xu, Guangzhou (CN); Pei Yu, Guangzhou (CN); Yewei Sun, Guangzhou (CN); Zaijun Zhang, Guangzhou (CN); Gaoxiao Zhang, Guangzhou (CN); Peng Yi, Guangzhou (CN)

( * ) Notice: Subject to any disclaimer, the term of this patent is extended or adjusted under 35 U.S.C. 154(b) by 0 days.

(21) Appl. No.: 15/732,636

(22) PCT Filed: Jul. 4, 2016

(86) PCT No.: PCT/CN2016/000359
§ 371 (c)(1),
(2) Date: Dec. 6, 2017

(87) PCT Pub. No.: WO2016/201957
PCT Pub. Date: Dec. 22, 2016

(65) Prior Publication Data
US 2018/0147181 A1    May 31, 2018

(30) Foreign Application Priority Data
Jun. 15, 2015 (CN) .......................... 201510329808.9

(51) Int. Cl.
*A61K 31/385* (2006.01)
*A61P 1/00* (2006.01)
*A61P 29/00* (2006.01)

(52) U.S. Cl.
CPC .............. *A61K 31/385* (2013.01); *A61P 1/00* (2018.01); *A61P 29/00* (2018.01)

(58) Field of Classification Search
CPC ........... A61K 31/385; A61P 1/00; A61P 29/00
See application file for complete search history.

(56) References Cited

PUBLICATIONS

Zhang et al., Journal of Translational Medicine, "Hypoglycemic and beta cell protective effects of andrographolide analogue for diabetes treatment", 2009, 7:62, 13 pages.*
Atreya et al., "NF-κB in inflammatory bowel disease", Journal of Internal Medicine, 2008, vol. 263, pp. 591-596.*
Liu et al., "Andrographolide sulfonate ameliorates experimental colitis in mice by inhibiting Th1/Th17 response", International Immunopharmacology, Apr. 4, 2014 (online publication), vol. 20, pp. 337-345.*

* cited by examiner

*Primary Examiner* — James D. Anderson
(74) *Attorney, Agent, or Firm* — Panterrain IP Law; Charles Liu

(57) ABSTRACT

The present invention provides uses of an andrographolide derivative in preparation of a medicament for preventing and treating inflammatory bowel disease. The andrographolide derivative AL-1 has the mechanisms, for the treatment of ulcerative colitis, of scavenging of free radicals, inhibition of NF-κB signaling pathway activation and COX-2 expression, activation of PPAR-γ expression, and thus can prevent the transcription and expression of inflammatory-related genes to improve the conditions of inflammation. AL-1 can be used as a medicine for the treatment of inflammatory bowel disease and can be formulated to various dosage forms with a pharmaceutically acceptable carrier.

6 Claims, 6 Drawing Sheets

USE OF ANDROGRAPHOLIDE DERIVATIVES IN PREPARATION OF MEDICAMENTS FOR PREVENTING AND TREATING INFLAMMATORY BOWEL DISEASES

FIELD OF THE INVENTION

The present invention relates to the field of medicines, and more particularly relates to use of andrographolide derivatives in preparation of medicaments for treating inflammatory bowel diseases such as ulcerative colitis.

BACKGROUND OF THE INVENTION

Andrographolide (Andro) is a main active component of traditional Chinese medicine Andrographis, and the structure of andrographolide is as shown below. Andrographis has been widely used in many Asia countries such as China, India, Japan, Korea for the treatment of inflammatory diseases including rheumatic arthritis, pharyngolaryngitis, diarrhea, and bacterial and viral infections. (Chin. Med. J. (Engl) 1991, 104: 770-775; J. Nat. Prod. 1993, 56: 995-999; Clin. Exp. Pharmacol. Physiol. 1996, 23: 675-678; Clin. Exp. Pharmacol. Physiol. 2000, 27: 358-363; Br. J. Pharmacol. 2002, 35: 399-406). Andrographolide can be used to alleviate clinical symptoms of inflammation, fever, bacteria and virus infectious diseases (J. Bacteriol. 2001, 183: 7126-7134).

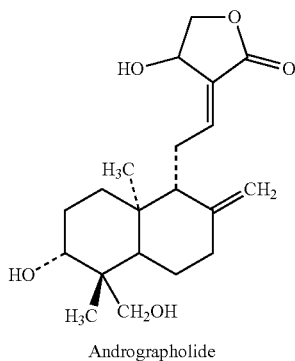

Andrographolide

Chiou et el. (Br. J. Pharmcol. 2009, 129: 1553-1560) found from research that andrographolide may inhibit NO synthesis in RAW 264.7 cells via reducing protein expression of inductible NO synthase (iNOS), and prevent de novo synthesis and reduce the stability of iNOS protein by accelerating degradation. Shen et al. (Br. J. Pharmacol. 2002, 135: 399-406) illustrated that the mechanism of andrographolide in inhibition of inflammatory reaction in neutrophilic granulocyte is to prevent or partially prevent the generation of active oxygen (ROS) by regulating PKC dependency, and suppress the high expression of MAC-1. Xia (J. Immunol. 2004, 173: 4207-4217) found from research that andrographolide inhibits the activity of NF-κB. Hidalgo et al. (Br. J. Pharmacol. 2005, 144: 680-686) showed from their research on anti-inflammatory mechanism of andrographolide that andrographolide has an anti-inflammatory effect by inhibiting the combination of NF-κB and DNA, so as to suppress the expression of proinflammatory proteins such as COX-2 and the like.

The inventors of this application have prepared coupling compounds of andrographolide and lipoic acid via chemical synthesis, i.e., the andrographolide derivative AL-1 (shown below).

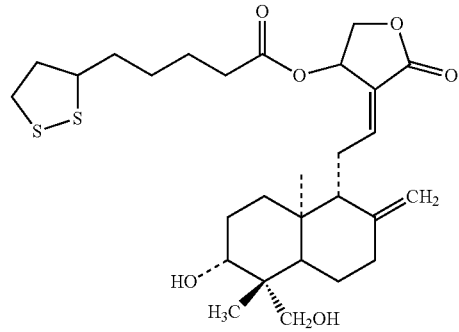

The inventors of this application demonstrated the research on the mechanism of AL-1 that, as AL-1 and Andro are applied respectively to react with GSH in vitro, the binding rate of AL-1 during the first 60 minutes of the reaction with the sulfydryl group of GSH is 7 times of that of Andro, which showed that the combination of AL-1 with the cysteine sulfydryl group of GSH is faster and stronger than that of Andro (Molecules. 2012, 17(1):728-739). Subsequent vitro cell experiments indicated that, by inhibiting the activity of NF-κB, AL-1 has the effect of protecting $MPP^+$-induced SH-SY5Y and mouse primary neuronal cells as well as IL-1β and IFN-γ-induced islet RIN-m cells (Pharmacol Biochem Behav. 2014, 122: 191-202; J Transl Med. 2009, 7: 62); animal experiments confirmed that AL-1 improves the behavioral indicators of MPTP-induced Parkinsonian mice by inhibiting the activity of NF-κB (Pharmacol Biochem Behav. 2014, 122: 191-2022), and also significantly improves the insulin resistance of the 2-type diabetic rats and inhibits phosphorylation of RIN-m-induced p65 and IκBα (Br J Pharmacol. 2015, doi: 10.1111/bph.13118); and therefore, it is shown that AL-1 is suitable to be used as an anticancer drug or as a drug against drug-resistant tumors, as an antimicrobial drug including that for against bacterial and viral infections, and as an antidiabetic drug. The inventors of this application found also the use of AL-1 in manufacture of medicaments for the prevention and treatment of neurodegenerative diseases including particularly Parkinson's disease.

SUMMARY OF THE INVENTION

The present invention showed on the basis of extensive exploration of the functions of the andrographolide derivative that AL-1, through reduction of the concentration of MPO in colon tissue, can suppress the expression of inflammatory cell cytokines TNF-α, IL-6 and IL-1β, suppress the expression of COX-2 and nuclear transcription factor NF-κB, stimulate the expression of PPAR-γ, and then prevent the transcription and expression of inflammation-related genes and improve the conditions of inflammation. Accordingly, the present invention provided that AL-1 can be used for the treatment of ulcerative colitis, and the research proved that the AL-1 can remarkably improve the conditions of injury of colon mucosa in ulcerative colitis mice and alleviate the symptom of colitis. This is a new use of AL-1 not funded in earlier stage of the research for treating diseases.

Ulcerative colitis (UC) is a chronic non-specific intestinal inflammatory disease the pathogeny of which is still not clear. The Lesions are usually first involving the rectum, and gradually spread to the whole colon, showing continuing diffuse inflammation in the colon mucosa and submucosa. The pathogenesis of the disease has not yet been fully understood, but is generally considered to be the result of multi-factorial interactions, including environmental, genetic, infectious and immune factors. The latest research in 2014 confirmed that, varying in different regions of the world, the annual incidence rate of UC was found to be about 0.5-31.5 per 100,000 people. The disease is complicated in its etiology, with long duration, difficult to cure, often recurrent, and possible to cause cancer. Therefore, further in-depth study on the pathogenesis and treatment of UC has important clinical significance and social value for the prevention and treatment of the disease.

The pathogenesis of UC is though not yet very clear at the present, but it is considered to be related to oxidative stress, inflammation and cell apoptosis. Therefore, the compounds with anti-oxidative, anti-inflammatory and anti-apoptotic activities may have protective effect on inflammatory colon, and may delay the course of ulcerative colitis. There are mainly three types of conventional medicines for treating UC: aminosalicylates, adrenal cortical hormones and immunosuppressive agents; the first type is long in medication cycle, poor in patient compliance and high in reoccurrence; and the second and third types have more adverse effects, and are easy to induce drug-dependence or intolerance. Therefore, the present invention certainly provided a novel method and new medication for the treatment of ulcerative colitis.

The present invention is directed to provide a novel method of an andrographolide derivative, i.e., AL-1, in the prevention and treatment of inflammatory bowel disease, in particular for preventing and treating ulcerative colitis.

The present invention is also directed to provide a use of the andrographolide derivative AL-1 in preparation of a medicament for preventing and treating inflammatory bowel disease.

The present invention shows that the andrographolide derivative AL-1 has the mechanisms for the treatment of ulcerative colitis of scavenging of free radicals, inhibition of NF-κB signaling pathway activation and COX-2 expression, activation of PPAR-γ expression, and thus can prevent the transcription and expression of inflammatory-related genes to improve the conditions of inflammation.

The andrographolide derivative AL-1 can be prepared can be prepared with a pharmaceutically acceptable carrier into various dosage forms, wherein the dosage forms may be, for example, tablets, granules, injections, powder, capsules or suspensions.

The medicaments of the andrographolide derivative for preventing and treating ulcerative colitis can be prepared based on conventional processes for various dosage forms. Pharmaceutically acceptable excipients and additives, which can be uses in the manufacture processes, may include, for example, compatible nontoxic fillers, binders, disintegrants, buffers, preservatives, antioxidants, lubricants, flavoring agents, thickening agents, colorants, emulsifiers or stabilizers.

AL-1 can be prepared into various dosage forms, including solid, semi-solid, and liquid and aerosol forms (Remington's Pharmaceutical Sciences, Mack Publishing Company (1995), Philadelphia, PA, 19th ed). In particular, the dosage forms may include, for example, tablets, pills, dragees, granules, gels, ointments, solutions, suppositories, injections, inhalants, and sprays. Such dosage forms can be used for topical and systemic administration and for immediate or sustained administration. The routes of administration, in addition to those mentioned above, include also oral, buccal, rectal, peritoneal, intraperitoneal, epicutaneous, subcutaneous and intratracheal administrations.

For injection administration, the compounds of AL-1 as described herein may be formulated as a solution, suspension or emulsion in a water-soluble or lipid-soluble solvent. In particular, the lipid-soluble solvent can be, for example, vegetable oils and the like, synthetic fatty glycerides, high fatty acid esters, and proylene glycols. The compound is preferably formulated in an aqueous solution, such as Hank's solution, Ringer's solution or physiological saline buffer solution.

For oral administration, the compounds of AL-1 as described herein may be formulated into a complex with pharmaceutically acceptable an excipient by conventional processes. With such excipient, the compound can be formulated into different dosage forms suitable for administration to a patient in need, and the dosage forms can be, for example, tablets, pills, suspensions, gels and the like. The dosage forms for oral administration can be prepared in a variety of processes, for example, in which the compound is mixed with a solid excipient, and the mixture is grinded, followed by addition of appropriate additives to produce granules. The additives that can be used to prepare oral dosage forms may include, for example, sugars such as lactose, sucrose, mannitol or sorbitol; celluloses such as corn starch, wheat starch, potato starch, gelatin, gum yellow, methylcellulose, hydroxyproylmethyl-cellulose, carboxymethylcellulose, polyvinylpyrrolidone and the like.

The compounds of AL-1 as described herein may be formulated into a spray agent, which can be prepared by using a presser and a nebulizer or a dry powder inhaler. Suitable propellants to be used in an injector may be, for example, dichlorodifluoromethane, fluorochloroform, dichlorotetrafluoroethane, carbon dioxide and dimethyl ether. The dosage amount of the aerosol can be adjusted by using an ejection valve.

The dosage forms as described herein are all related to the therapeutically effective amount of the compounds of the invention. The therapeutically effective amount of the compounds as described herein may depend on specific conditions of patients under the treatment. To determine the appropriate dose, various factors much be taken into account, for example, the route of administration to be used, weight and conditions of the patient to be treated, and observation and subjective judgment made by the prescribing physician. The therapeutically effective amount is usually determined by an experienced prescribing physician.

Oxidative stress, inflammatory reaction and NF-κB activation play an important role in the development of ulcerative colitis. The andrographolide derivative as described herein can inhibition of NF-κB signaling pathway activation and COX-2 expression, activation of PPAR-γ expression, and thus can prevent the transcription and expression of inflammatory-related genes for treating ulcerative colitis.

Figure 1:
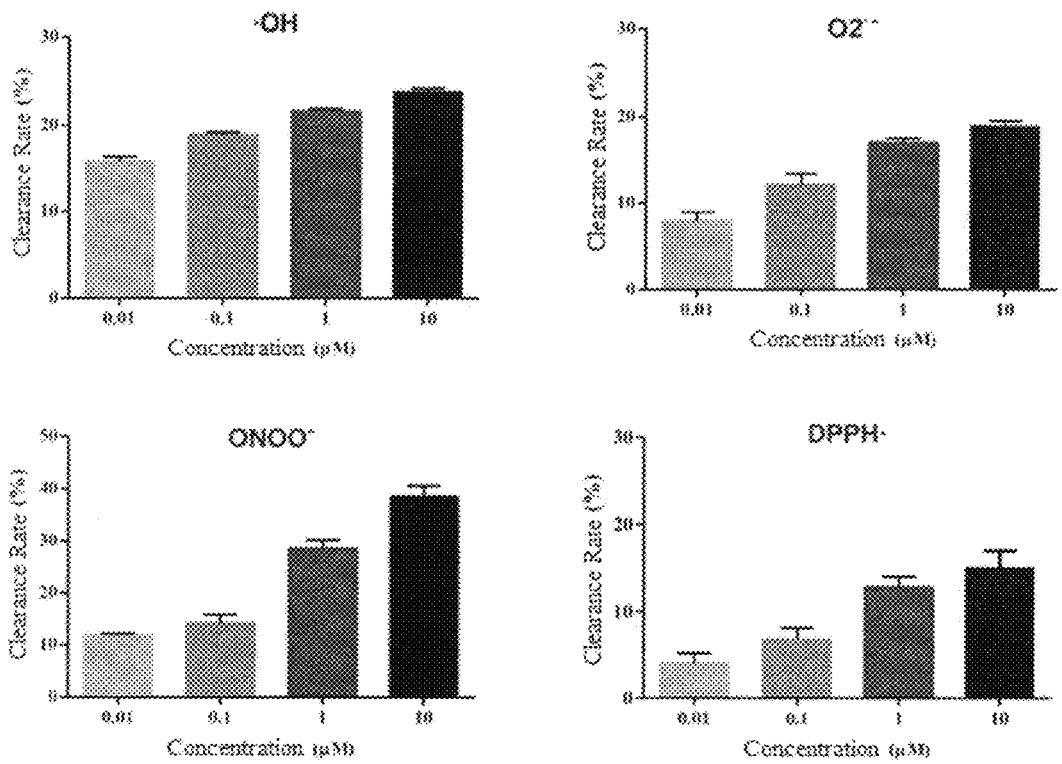
FIG. 1 shows the in vitro scavenging effects of AL-1 to hydroxyl radical (·OH), superoxide anion radical (O2$^{-}$·), peroxynitrite anion (ONOO$^{-}$) and 1,1-diphenyl-2-phenylhydrazine free radical (DPPH).

As shown in the drawings, the characters "#", "##", "*" and "**" are used to describe the level of statistical significance of test results as commonly known by a person of skills in the art, for example, # $p<0.05$, ## $p<0.01$, ### $p<0.001$, * $p<0.05$,  $p<0.01$, * $p<0.001$, wherein "*" is used for Control, and "#" is used for Model.

DETAILED DESCRIPTION OF THE EMBODIMENTS

The following examples are intended for illustration only and are not intended to restrict the scope of the present invention in any way.

Example 1. In Vitro Free Radicals Scavenging Effects of AL-1 to Hydroxyl Radical (·OH), Superoxide Anion Radical ($O_2^{-}$·), Peroxynitrite Anion (ONOO⁻) and 1,1-Diphenyl-2-Phenylhydrazine Free Radical (DPPH)

Hydroxyl radicals (·OH): The hydroxyl radicals were generated by using phenanthroline-metal ions-$H_2O_2$ via Fenton reaction ($H_2O_2 + Fe^{2+} \rightarrow ·OH + H_2O + Fe^{3+}$), which promotes the phenanthroline-$Fe^{2+}$ being oxidized to phenanthroline-$Fe^{3+}$, resulting in maximal disappearance at 440 nm in aqueous solution, which is used to calculate the clearance rate. Specifically, in a 48-well plate were added with 300 μL of double-distilled water (blank control) or AL-1 in different concentrations (prepared by dissolving in DMSO to 10 mM stock solution and then being diluted to 0.01 μM, 0.1 μM, 1 μM and 10 μM), added with 50 μL of 1.0 mM o-phenanthroline (1.0 mM dissolved in 50 mM NaCl), added respectively with 125 μL of 1.0 mM $H_2O_2$ and 125 μL of 2.0 mM $Fe^{2+}$ and mixed, and then the percentage of absorbance reduction at 440 nm in 100 seconds was measured by using a BioTek Synergy HT microplate reader. The hydroxyl radical scavenging rate is calculated as follows: Clearance rate (%)=$[1-(A_0-A_{100})/A_0] \times 100\%$, wherein $A_0$ and $A_{100}$ are the absorbance values at 0 and 100 seconds, respectively.

Superoxide anion radicals ($O_2^{-}$·): The radicals were prepared by pyrogallol autoxidation method, specifically including: in a 48-well plate were added respectively with 250 μL of 50 mM Tris-HCl buffer solution (pH 8.2), 300 μL of double distilled water (blank control) or AL-1 in different concentrations (dissolved in DMSO to 10 mM stock solution and then diluted to 0.01 μM, 0.1 μM, 1 μM, 10 μM with double distilled water), and then 50 μL of 2.0 mM pyrogallol was added and mixed with a vortex mixer. Blank controls were used to record the absorbance at 320 nm for every 30 seconds, and absorbance was measured for 30 min by using a BioTek Synergy HT microplate reader. The absorbance of the samples was measured under the same conditions. The rate of oxidation was defined as the increasing value of the absorbance per minute. Linear regression method: the graph was made with time (second) as the horizontal coordinate and absorbance value as the vertical coordinate, the linear relationship between absorbance value and time was obtained, the result of the pyrogallol autoxidation rate was shown as dA/dt, the increment of absorbance value per second, i.e., the value a in R2 of the linear regression equation y=ax+b. Clearance rate (%)=(dA/dt−dAs/dt)/(dA/dt), wherein, dA/dt is the autoxidation rate of pyrogallol in the absence of sample, and dAs/dt is the autoxidation rate of pyrogallol in the presence of sample.

Peroxynitrite anion (ONOO⁻): SIN-1 decomposes in a weak alkaline condition (PBS pH 7.4) and can simultaneously produce superoxide anion radicals ($O_2^{-}$·) and nitric oxide radicals (NO·), which instantly produce peroxynitrite anion (ONOO⁻). ONOO− reacts with and oxidizes luminol to emit light at 425 nm. In particular, the test was run in the steps as follows: To a 96-well black opaque ELISA plate using a micropipette was added sequentially a solution of 60 μL 0.1 mol/L PBS (pH=7.4), AL-1 in different concentrations (10 mM stock solution with DMSO, being diluted with double-distilled water to 0.01 μM, 0.1 μM, 1 μM, 10 μM) or 0.1 mol/L PBS (pH=7.4) solution (control group), 20 μL 1.0 mmol/L Luminol solution and 20 μL 3 mg/mL SIN-1 hydrochloride solution were added in well mode by using a liquid injector. The total kinetic mode time is 00:33:20 and the time interval is 00:01:40. The ONOO⁻ generation was judged by luminous intensity. Antioxidant (AH) competed with luminol (L) to react with ONOO⁻, to cause reduction of the reaction between ONOO⁻ and LH— and the light intensity as well. The light intensity is shown to be inversely related to the capacity of the antioxidant. The light intensity is recorded on a chemiluminescence instrument at set time intervals. The clearance rate is used to describe the ability of the antioxidant to capture ONOO⁻.

$$\text{Clearance rate } (\%) = (A_{ctrl} - A_{sample})/A_{ctrl} \times 100\%.$$

1,1-Diphenyl-2-phenylhydrazine free radicals (DPPH): The spectrophotometric measurement of 1,1-Diphenyl-2-phenylhydrazine free radicals (DPPH) is based on a strong absorption of DPPH at 517 nm, and a methanol solution of DPPH is shown in dark purple color. In the presence of a free radical scavenger, the absorption disappears due to electron pairing, and the degree of color fading is quantitatively related to the number of electrons accepted by DPPH. The change in absorption can be used for quantitative analysis. Thus, based on detection of absorption change of the samples in different concentrations, clearance rate can be used to indicate the strength of the scavenger. The specific test may include the following steps: To a 96-well plate were added with 100 μL of sample solution in different concentrations (sample group) or 100 μL of methanol (blank control group), and then 100 μL solution of 100 μM DPPH in methanol (final concentration of 50) was added, with 3-5 replicate wells for each of the samples. The samples were shaken evenly and placed one hour at room temperature under dark conditions, and then the absorbance was measured at 517 nm with a microplate reader. The clearance rate is calculated as: Clearance rate (%)=$(A_{ctrl} - A_{sample})/A_{ctrl} \times 100\%$.

The in vitro scavenging effect of AL-1 to hydroxyl radical (·OH), superoxide anion radical ($O_2^-$·) peroxynitrite anion ($ONOO^-$) and 1,1-diphenyl-2-phenylhydrazine free radical (DPPH) are shown in FIG. 1.

Figure 2:
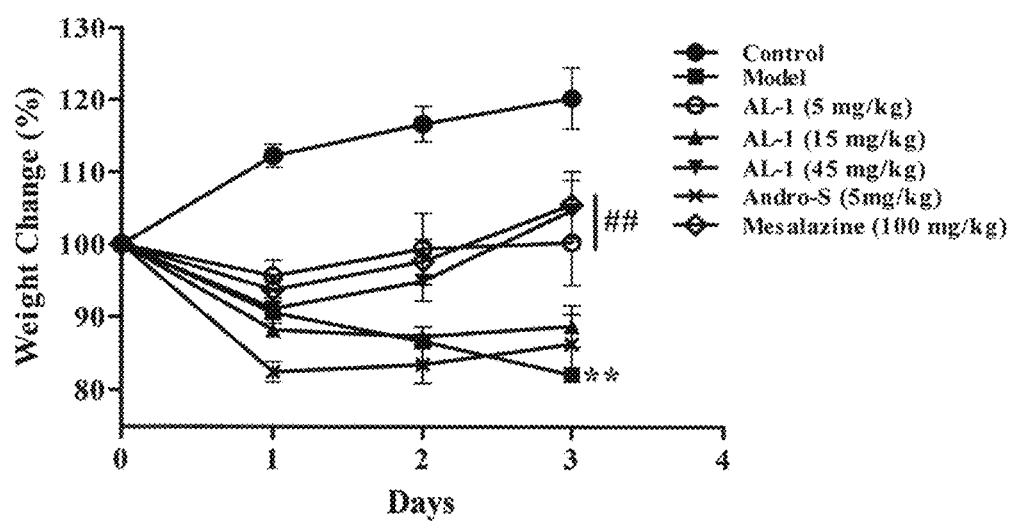
FIG. 2 shows the effects of AL-1 on body weight of TNBS-induced ulcerative colitis mice.

Example 2. Effect of AL-1 on the Body Weight of TNBS-Induced Ulcerative Colitis Mice The mice of normal control group were shown lively, body hair shiny, and weight continued to increase. The model mice after TNBS enema appeared to be apathetic and lazy with body hair messy and less luster, and with water intake being reduced. The model mice were also shown continuing decrease in body weight, with an average weight loss of 17.9% on the third day compared with that before rectal perfusion. The mice in AL-1 and Mesalazine groups showed less symptoms than those in the TNBS group; after a slight decrease in body weight on the first day, body weight rose from the second day, and, on the third day, the body weight of the mice being administered with AL-1 (45 mg/kg) increased by 4.65% on average compared with that of the model group, and the activity behavior also showed improvement as compared to the model mice. From the second day after modeling, Mesalazine also significantly increased body weight of the mice ($P<0.05$). The effects of AL-1 on the body weight of TNBS-induced ulcerative colitis mice is shown in FIG. 2.

Figure 3:
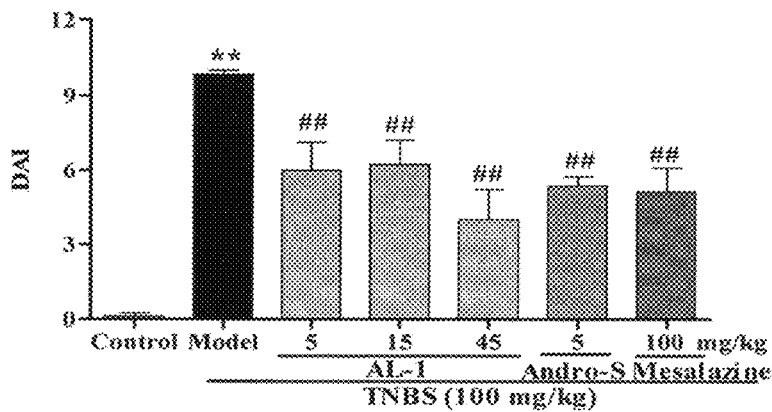
FIG. 3 shows the effects of AL-1 on disease activity index scores of the TNBS-induced ulcerative colitis mice.

Example 3. Effects of AL-1 on Disease Activity Index (DAI) of TNBS-Induced Ulcerative Colitis Mice On the third day after enema, seven of the mice in TNBS group showed loose stools, and some of them showed visible bloody stools. The occult blood test results were all strongly positive and the body weight was significantly reduced with an average DAI score of 9.86; the average DAI score for the AL-1 (5 mg/kg) group was 6.00, for the AL-1 (15 mg/kg) group was 6.25, for the AL-1 (45 mg/kg) group was 4.00, and for the Mesalazine (100 mg/kg) group was 5.13. The DAI scores of the above groups were significantly lower than those of the model group and the difference were very significant ($P<0.01$); the DAI score of the AL-1 (45 mg/kg) was lower than that of the Mesalazine group. Disease activity index scores of the TNBS-induced ulcerative colitis mice are shown in FIG. 3.

Figure 4:
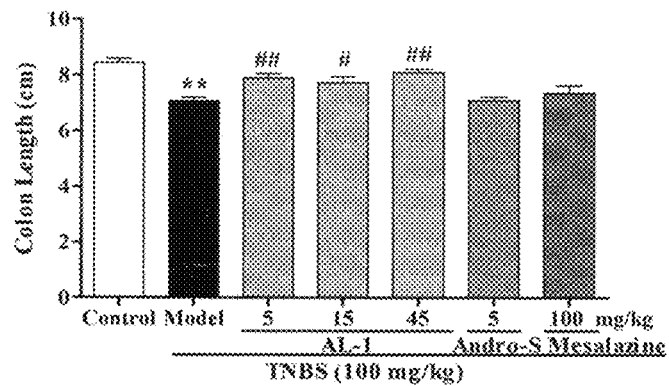
FIG. 4 shows the effects of AL-1 on the colon length of the TNBS-induced ulcerative colitis mice.

Example 4. Analysis of the Effects of AL-1 on the Colon Length of the TNBS-Induced Ulcerative Colitis Mice Three days after TNBS enema, the mice in each experimental group were sacrificed and dissected, the colon was removed and the intestinal tract was washed with cold PBS, and then the damage of colonic inflammation was observed with the length of the colon being measured. The results of anatomy showed that the model group mice had significant expansion in the colon, thinning of the intestinal wall, severe congestion, edema, ulcers with surface erosion in the intestinal mucosa, significant deformation and shortening of the intestine due to inflammatory exudation, bleeding and scar healing of the intestinal tube. The AL-1 (5, 15 and 45 mg/kg) groups showed significant improvement on TNBS-induced inflammatory exudation, hemorrhage and scarring in the colon of mice, thereby enhanced the colonic length in the mice. The effect of Mesalazine on the improvement of colon length was not significant, and indicated with no statistical difference as compared with the model groups. The results of the analysis of the colon length of the mice in each group are shown in FIG. 4.

Figure 5:
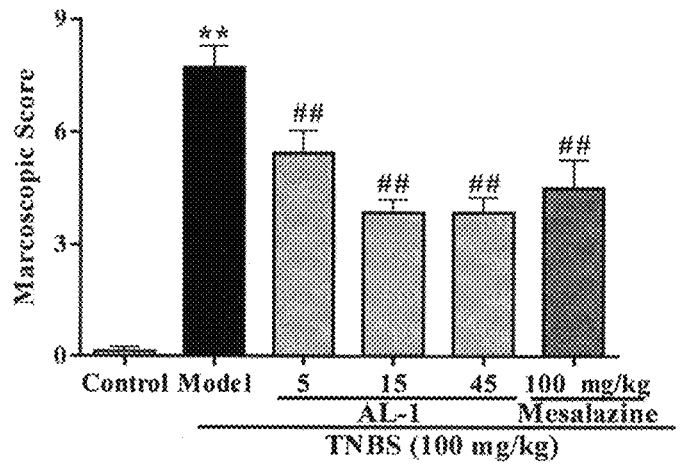
FIG. 5 shows the morphological observation of AL-1 on the colon of the TNBS-induced ulcerative colitis mice.

Example 5. Morphological Observation of AL-1 on the Colon of the TNBS-Induced Ulcerative Colitis Mice The morphological observation of the mice colon indicated that the colon anatomical structure of the in normal mice is clear with thin and smooth intestinal wall, and there was no mucosal hyperemia and no bleeding and ulcer changes. In the TNBS model group mice, the lesions of the colon were obvious, the colon was shortened, the proximal colon was dilated with indication of obstructive lesions, and the distal intestine became narrowed with indication of ulceration with congestion, edema, erosion and intestinal wall thickening. The AL-1 (5, 15 and 45 mg/kg) groups showed significant reduction of the symptoms of the TNBS-induced colitis mice, increased length of the colon, improved intestinal ulcer and edema, and alleviated intestinal wall thickening and congestion. The Mesalazine group also showed improvement on colon injury of the TNBS-induced mice. The general colonic morphology scores of the model groups were significantly higher than that of the other groups ($P<0.01$). The morphological observation of the colon of the TNBS-induced ulcerative colitis mice is showed in FIG. 5.

Figure 6:
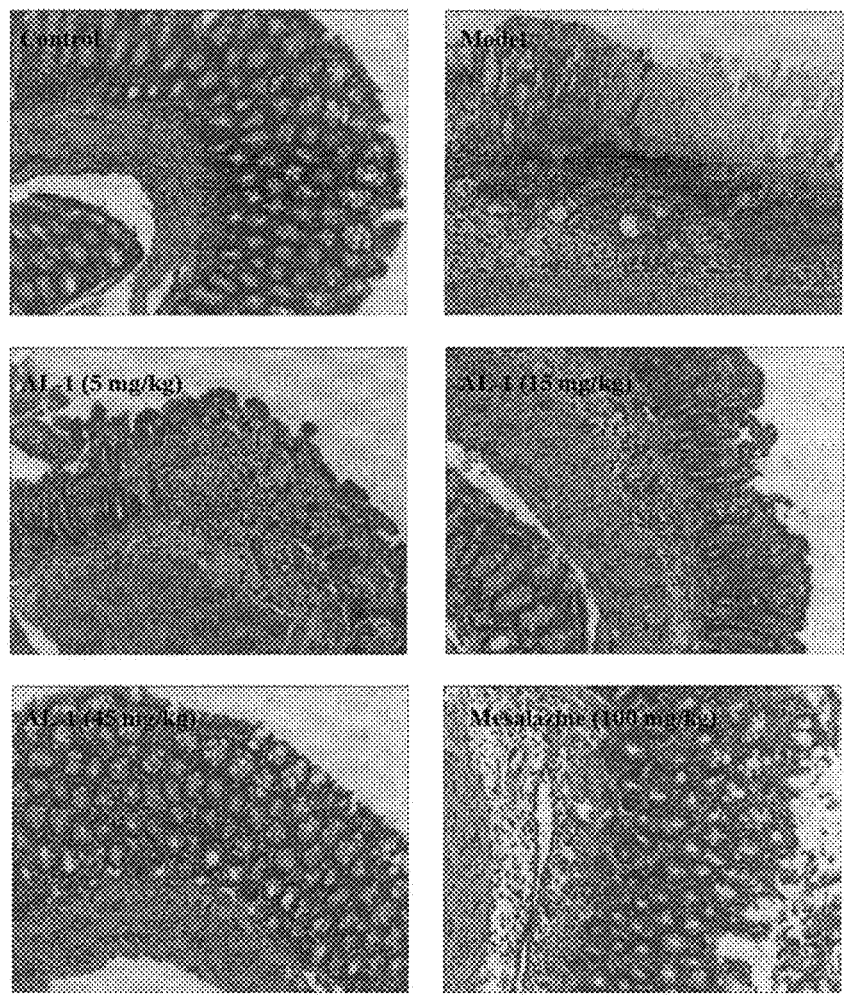
FIG. 6 shows the histopathological observation of AL-1 on the colon of the TNBS-induced ulcerative colitis mice.
Figure 6:
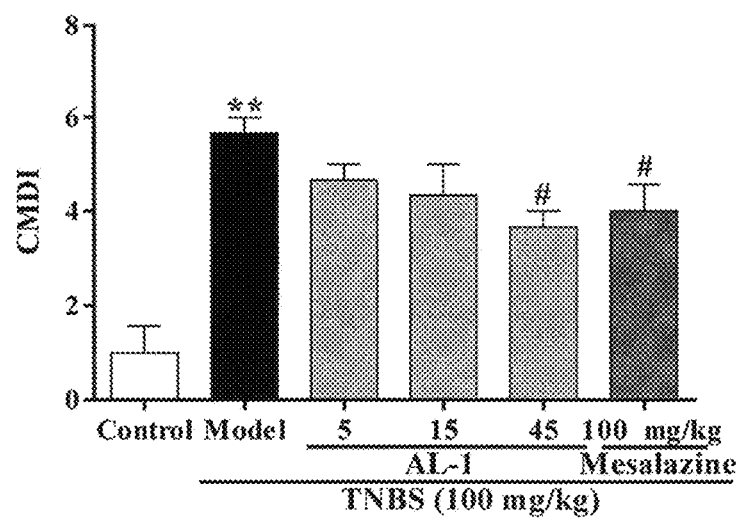

Example 6. Histopathological Observation of AL-1 on the Colon of the TNBS-Induced Ulcerative Colitis Mice Colon tissues were paraffin-embedded and sliced in parallel with HE staining. The results showed that the colon of mice in normal control group had intact colon structure, no infiltration of inflammatory cells, clear intestinal mucosa and normal cell morphology. The model groups showed much inflammatory cell infiltration in mucosa, submucosa and muscularis, a large number of lymphocytes gathered together to form lymphoid follicles, and significant missing or necrotic intestinal mucosa, irregular glandular arrangement and vascular congestion and expansion. The AL-1 (5 mg/kg) group showed obvious myositis cell infiltration of mucosa and submucosa but in much less extent as compared with the model groups, and some irregularity in the glandular arrangement. The AL-1 (15 mg/kg) group still showed some myositis cell infiltration of mucosa and submucosa, but the myositis cell infiltration was reduced, and the deficiency of glands was significantly less than that of the model group, and the glandular arrangement is more regular. The AL-1 (45 mg/kg) group showed significant reduction in the amount of myositis cell infiltration of mucosa and submucosa, the mucosal structure was clear, the glandular arrangement was regular, and the cellular morphology was normal. The Mesalamine (100 mg/kg) group showed obvious relief of myositis cell infiltration, but the infiltration of inflammatory cells in the submucosa and mucosa was still obvious, the degree of glandular defects was significantly reduced as compared with the model group, the arrangement of gland was more regular and the tissue damage was improved. The results of CMDI also showed that AL-1 (5, 15 and 45 mg/kg) could improve tissue damage in a dose-dependent manner, and Mesalazine also had significant effect to improve mucosal injury in mice. Histopathological observation of the colon in each of the groups is shown in FIG. 6.

Figure 7:
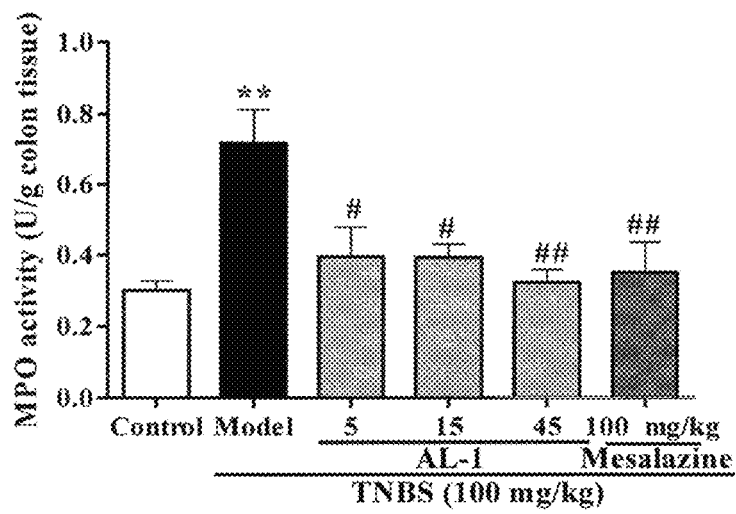
FIG. 7 shows the effect of AL-1 on myeloperoxidase (MPO) activity in colon tissue of the TNBS-induced ulcerative colitis mice.

Example 7. Effect of AL-1 on Myeloperoxidase (MPO) Activity in Colon Tissue of the TNBS-Induced Ulcerative Colitis Mice It can be seen from the results of MPO activity test in colonic tissues that the content of MPO in normal tissue was very low, the neutrophil infiltration was obvious in model group treated with TNBS, and the content of MPO increased obviously, being twice as that in normal group. The AL-1 (5, 15 and 45 mg/kg) group could lessen in a dose-dependent manner the increase of the MPO content in the colon tissue of mice induced by TNBS. Mesalazine can also obviously reduce the content of MPO with the difference being significant (P<0.01). The effect of AL-1 on MPO activity in colon tissue of the mice is shown in FIG. 7.

Figure 8:
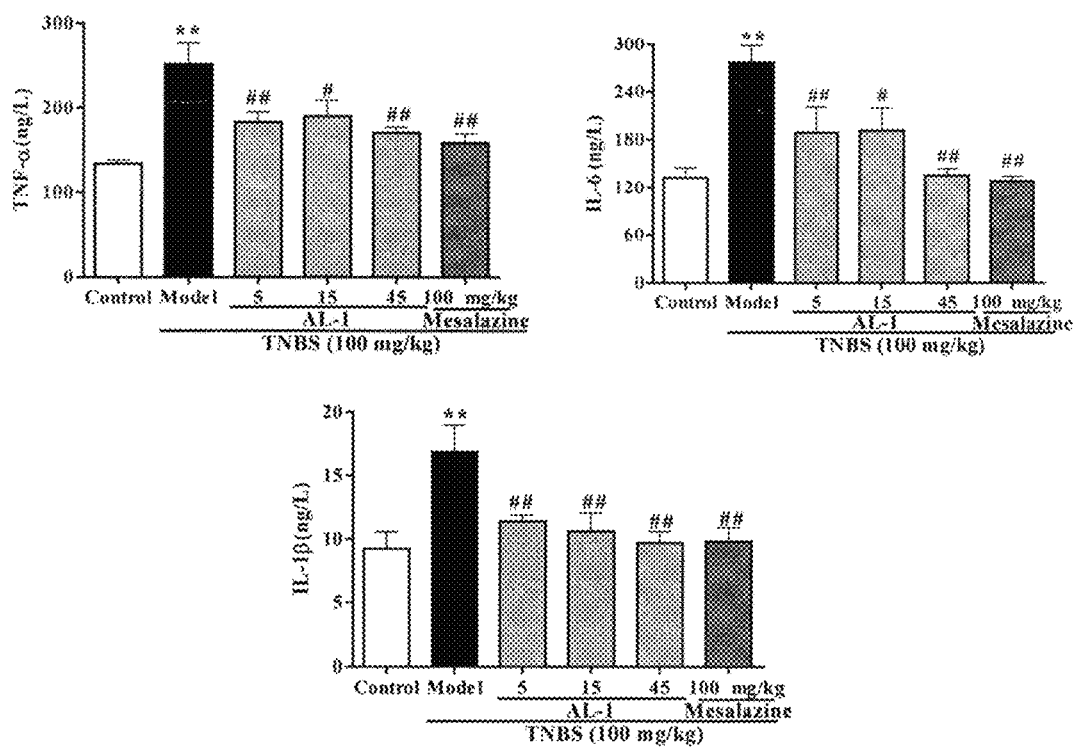
FIG. 8 shows the effect of AL-1 on the activity of serum inflammatory cytokines (TNF-α, IL-1β, IL-6) in the TNBS-induced ulcerative colitis mice.

Example 8. Effect of AL-1 on the Activity of Serum Inflammatory Cytokines (TNF-α, IL-1β, IL-6) in the TNBS-Induced Ulcerative Colitis Mice After TNBS modeling, the levels of three inflammatory factor of TNF-α, IL-6 and IL-1β were significantly increased, wherein the TNF-α level increased by about 1.5-fold, the IL-6 level increased by about 2-fold, and the IL-1βlevel also increased about 2-fold. However, the treatments of AL-1 (5, 15, 45 mg/kg) and Mesalazine can significantly lessen the increase in the serum levels of these inflammatory factors in TNBS-induced mice, with the difference being significant. The effect of AL-1 on the activity of serum inflammatory cytokines (TNF-α, IL-1β, IL-6) in mice is shown in FIG. 8.

Figure 9:
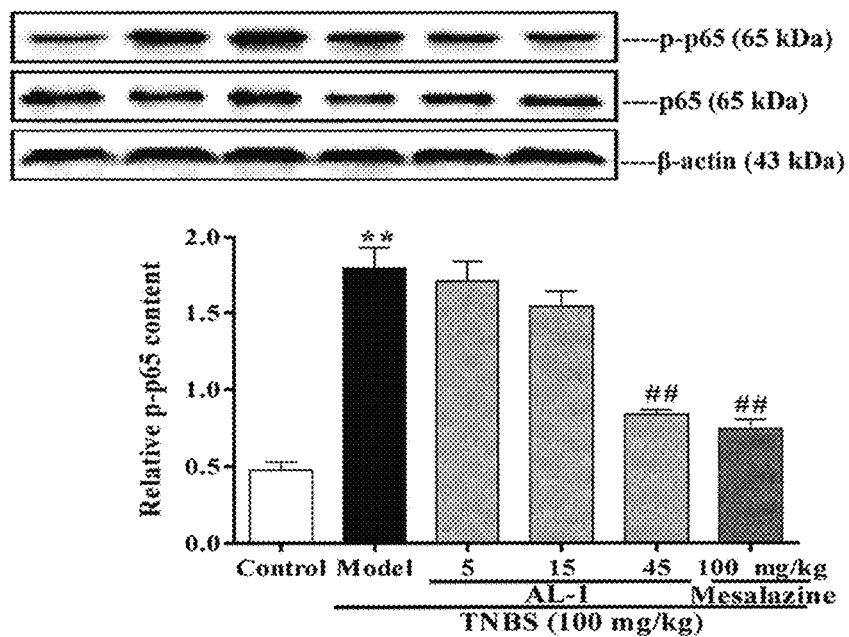
FIG. 9 shows the effect of AL-1 on the activation of the p65 subunit in the NF-κB signaling pathway in colon tissue.

Example 9. Effect of AL-1 on the Activation of the p65 Subunit in the NF-κB Signaling Pathway in Colon Tissue NF-κB, as a key transcription factor regulating the release of inflammatory cytokines, plays an important role in the complex cytokine dysregulation network of IBD. To investigate whether the inhibitory effect of AL-1 on the expression of inflammatory cytokines TNF-α, IL-6 and IL-1β is related to the activation of NF-κB signaling pathway, the present inventors used Western blotting to detect the expression of p-p65 and p65 in colonic tissues. The results showed that TNBS significantly increased the expression of p-p65 in NF-κB pathway in colonic tissue; compared with the model group, both AL-1 and mesalazine treatment groups could significantly reduce the phosphorylation level of p65, and thus has inhibitory effect on NF-κB pathway-related gene expression. The effect of AL-1 on the activation of the p65 subunit in the NF-κB signaling pathway in colon tissue is shown in FIG. 9.

Example 10. Effect of AL-1 on the Expression of COX-2 in Colon Tissue

Figure 10:
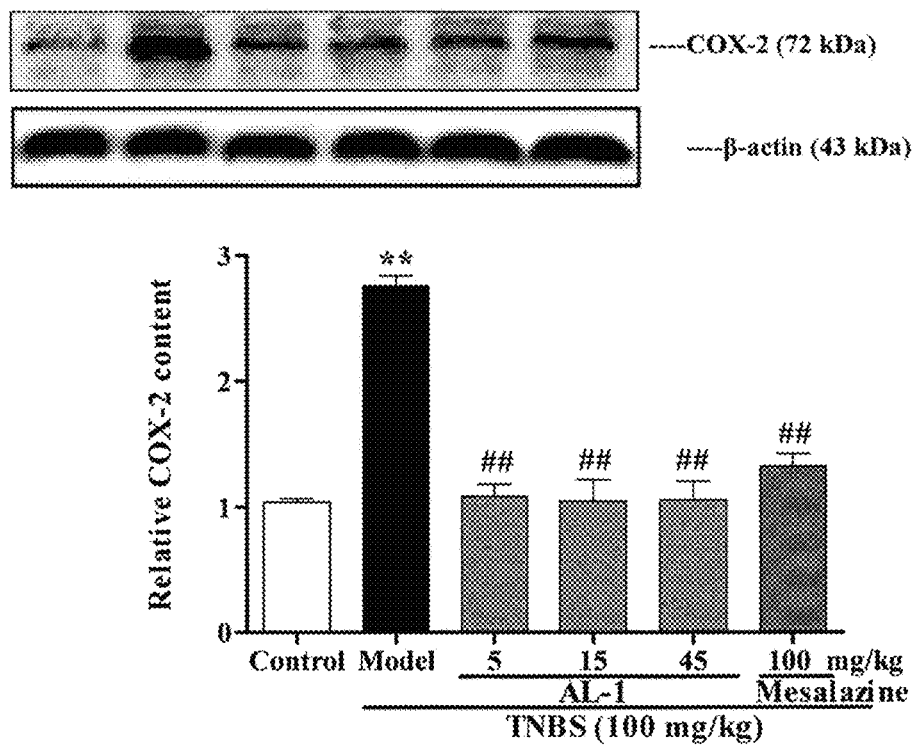
FIG. 10 shows the effect of AL-1 on the expression of COX-2 in colon tissue.

Cyclooxygenase-2 (COX-2) is undetectable in normal human colonic epithelial cells, but the presence of a large amount of COX-2 can be detectable in the intestinal mucosal epithelial cells of CD patients and UC patients. Such high expression can cause elevated expression of pro-inflammatory substance of prostaglandin, and promote IBD epithelial congestion and edema. The results of this experiment showed that TNBS had a significant effect of increasing COX-2 expression, which was about 2.5 times higher than that of normal group. However, administration of AL-1 and Mesalamine could effectively inhibit the increase of COX-2 expression level in the TNBS-induced mice. The effect of AL-1 on the expression of COX-2 in colon tissue is shown in FIG. 10.

Figure 11:
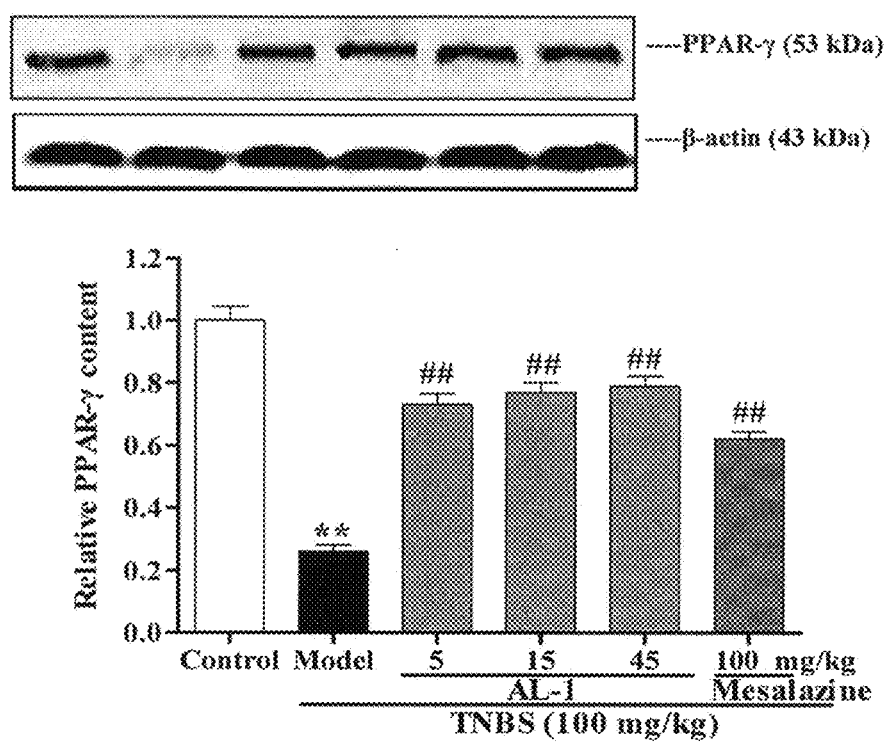
FIG. 11 shows the effect of AL-1 on the amount of PPAR-γ expressed in colon tissue.

Example 11. Effect of AL-1 on the Amount of PPAR-γ Expressed in Colon Tissue Peroxisome proliferator-activated receptor γ (PPAR-γ) may have anti-inflammatory effects by inhibiting the expression of transcription factors NF-κB, AP-1 and other related genes, have the effects of reducing the expression of inflammatory factors and adhesion molecules, and play important role for maintaining the integrity of the intestinal mucosa. Studies have shown that, when IBD occurred, the in vivo expression of PPAR-γ would be reduced in some extent. The results of this study showed that TNBS significantly reduced the expression of PPAR-γ in colon tissue, while AL-1 and Mesalamine significantly increased the expression of PPAR-γ, which suggests that AL-1 and Mesalamine may have anti-inflammatory effect through increasing the in vivo expression of PPAR-γ. The effect of AL-1 on the amount of PPAR-γ expressed in colon tissue is shown in FIG. 11.

Although particular embodiments have been herein described in detail, the above description has been done by way of example for purposes of illustration only, and is not intended to be limiting with respect to the scope of the appended claims which follow. In particular, it is contemplated by the inventor that various substitutions, alterations, and modifications may be made to the invention without departing from the spirit and scope of the invention as defined by the claims.

The invention claimed is:

1. A method of prevention and treatment of a disease, comprising administration of a therapeutically effective amount of an andrapholide derivative, wherein the andrapholide derivative has a structure of formula (AL-1):

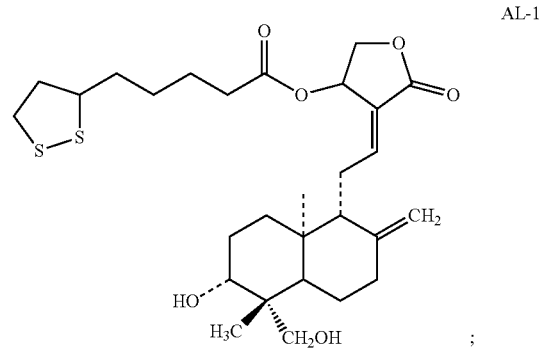

wherein, the disease is ulcerative colitis or Crohn's disease, and wherein, for the prevention and treatment of the disease, the andrapholide derivative has functions of reduction of concentration of MPO in colon tissue, suppression of expression of inflammatory cell cytokines TNF-α, IL-6 and IL-1β, suppression of expression of COX-2 and nuclear transcription factor NF-κB, stimulation of expression of PPAR-γ, and prevention of transcription and expression of inflammation-related genes.

2. The method according to claim 1, wherein the disease is ulcerative colitis.

3. The method according to claim 1, wherein the disease is Crohn's disease.

4. The method according to claim 1, wherein the andrographolide derivative is used alone or in combination with other drugs.

5. The method according to claim 1, wherein the andrographolide derivative is prepared with a pharmaceutically acceptable carrier.

6. The method according to claim 1, wherein the andrographolide derivative is prepared as a medicament in a dosage form of tablet, granule, injection, powder, capsule or suspension.

\* \* \* \* \*